United States Patent
Konishi et al.

(10) Patent No.: US 7,247,755 B2
(45) Date of Patent: Jul. 24, 2007

(54) PROCESS FOR PRODUCING α,α-BIS(HYDROXYMETHYL)ALKANAL

(75) Inventors: Shinichi Konishi, Yokohama (JP); Shingo Nakayama, Yokkaichi (JP); Yukihiro Isogai, Nagoya (JP); Tokuyuki Yoshimoto, Yokkaichi (JP)

(73) Assignee: Kyowa Hakko Chemical Co., Ltd., Tokyo (JP)

( * ) Notice: Subject to any disclaimer, the term of this patent is extended or adjusted under 35 U.S.C. 154(b) by 73 days.

(21) Appl. No.: 10/563,156

(22) PCT Filed: Jul. 22, 2004

(86) PCT No.: PCT/JP2004/010754

§ 371 (c)(1), (2), (4) Date: Jan. 4, 2006

(87) PCT Pub. No.: WO2005/007605

PCT Pub. Date: Jan. 27, 2005

(65) Prior Publication Data

US 2007/0112221 A1    May 17, 2007

(30) Foreign Application Priority Data

Jul. 23, 2003    (JP) .............................. 2003-200528

(51) Int. Cl.
*C07C 45/72*    (2006.01)
*C07C 51/16*    (2006.01)

(52) U.S. Cl. ...................... 568/460; 568/461; 568/464; 562/523; 562/531

(58) Field of Classification Search ............... 568/464; 562/531
See application file for complete search history.

(56) References Cited

U.S. PATENT DOCUMENTS 3,312,736 A * 4/1967 Ruhf .......................... 562/531
4,122,290 A * 10/1978 Immel et al. ................ 568/853
4,233,247 A * 11/1980 Immel et al. ................ 568/464
4,247,485 A * 1/1981 Immel et al. ................ 568/464
5,146,004 A * 9/1992 Morris et al. ................ 568/463
5,618,985 A   4/1997 Kulmala et al. ............. 568/853
5,994,592 A * 11/1999 Yokoyama et al. .......... 568/464

FOREIGN PATENT DOCUMENTS

| JP | 08-500615 | 1/1996 |
| JP | 11-209323 | 8/1999 |
| JP | 11-222453 | 8/1999 |
| JP | 11-228478 | 8/1999 |

\* cited by examiner

*Primary Examiner*—Sikarl A. Witherspoon
(74) *Attorney, Agent, or Firm*—Fitzpatrick, Cella, Harper & Scinto

(57) ABSTRACT

The present invention provides a process for producing an α,α-bis(hydroxymethyl)alkanal represented by Formula (II):

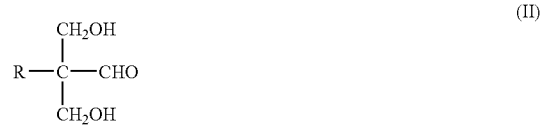

(wherein R represents an alkyl group, a cycloalkyl group, or an aryl group) which comprises reacting an aldehyde represented by Formula (I):

$$R-CH_2-CHO \qquad (I)$$

(wherein R has the same meaning as defined above) with formaldehyde in the presence of a basic catalyst and a phase-transfer catalyst.

10 Claims, No Drawings

PROCESS FOR PRODUCING α,α-BIS(HYDROXYMETHYL)ALKANAL

TECHNICAL FIELD

The present invention relates to a process for efficiently producing an α,α-bis(hydroxymethyl)alkanoic acid useful in producing polymers such as polyurethane, polyester, and epoxy resins and also relates to a process for efficiently producing an α,α-bis(hydroxymethyl)alkanal, an intermediate thereof.

BACKGROUND ART

As processes for producing an α,α-bis(hydroxymethyl)alkanal, a process for allowing an aliphatic aldehyde to react with formaldehyde in the presence of a basic catalyst is known. Examples of the basic catalyst used in the process include hydroxides such as sodium hydroxide, potassium hydroxide, and calcium hydroxide, containing an alkali metal or an alkaline-earth metal; carbonates, such as sodium carbonate, potassium carbonate, sodium hydrogen carbonate, and potassium hydrogen carbonate, containing an alkali metal or an alkaline-earth metal; tertiary amines; and solid basic catalysts such as basic ion exchangers (see, for example, Japanese Published Examined Patent Application No. 20965/1977, Japanese Published Unexamined Patent Application No. 263141/1987, Japanese Published Examined Patent Application No. 55181/1992, U.S. Pat. No. 3,312,736, and West Germany Patent No. 2,507,461).

In the production of the α,α-bis(hydroxymethyl)alkanal, the yield of the α,α-bis(hydroxymethyl)alkanal is low in general when the ratio of formaldehyde to the aliphatic aldehyde is less than or equal to a stoichiometric ratio, that is, the amount of formaldehyde used is 2 mol or less with respect to 1 mol of the aliphatic aldehyde. Therefore, processes in which two moles or more of formaldehyde is allowed to react with one mole of the aliphatic aldehyde are disclosed (see, for example, Japanese Published Unexamined Patent Application No. 135717/1979 and Japanese Published Examined Patent Application No. 55181/1992). However, the processes disclosed in these patent documents are not cost-effective because a large amount of formaldehyde remains after the completion of the reaction and complicated operations for separating and/or recovering the remaining formaldehyde must be performed. Furthermore, if a reaction product is subjected to a step such as an oxidation step or hydrogenation step without removing the remaining formaldehyde, the processes have problems such as a necessity for an excessive amount of reactants and a heavy load of a step of refining a product.

On the other hand, a process in which formaldehyde is allowed to react with an aliphatic aldehyde at a stoichiometric ratio is also disclosed (see, for example, Japanese Published Unexamined Patent Application No. 209323/1999). However, an example disclosed in this patent document shows that the conversion of formaldehyde is below 90% and a step of removing formaldehyde is necessary. If formaldehyde is not removed, there is a problem that the load of a refining step becomes heavy.

Accordingly, a process for producing for enhancing the conversion of formaldehyde to produce an α,α-bis(hydroxymethyl)alkanal efficiently has been demanded.

DISCLOSURE OF THE INVENTION

The present invention provides the following (1) to (8) below.

(1) A process for producing an α,α-bis(hydroxymethyl)alkanal represented by Formula (II):

(wherein R represents an alkyl group, a cycloalkyl group, or an aryl group) which comprises reacting an aldehyde represented by Formula (I):

(wherein R has the same meaning as defined above) with formaldehyde in the presence of a basic catalyst and a phase-transfer catalyst.

(2) The process for producing according to (1), wherein the amount of formaldehyde used is in the range of 0.3 to 1.7 mol with respect to 1 mol of the aldehyde represented by Formula (I).

(3) The process for producing according to (1) or (2), wherein the amount of the phase-transfer catalyst used is in the range of 0.0001 to 10 mol with respect to 1 mol of the basic catalyst.

(4) The process for producing according to any one of (1) to (3), wherein the phase-transfer catalyst is an onium salt, a crown ether, or a surfactant.

(5) The process for producing an α,α-bis(hydroxymethyl)alkanoic acid represented by Formula (III):

(wherein R represents an alkyl group, a cycloalkyl group, or an aryl group) which comprises reacting an aldehyde represented by Formula (I):

(wherein R has the same meaning as defined above) with formaldehyde in the presence of a basic catalyst and a phase-transfer catalyst to obtain an α,α-bis(hydroxymethyl)alkanal represented by Formula (II):

(wherein R has the same meaning as defined above) and oxidizing the obtained α,α-bis(hydroxymethyl)alkanal.

(6) The process for producing according to (5), wherein the amount of formaldehyde used is in the range of 0.3 to 1.7 mol with respect to 1 mol of the aldehyde represented by Formula (I).

(7) The process for producing according to (5) or (6), wherein the amount of the phase-transfer catalyst used is in the range of 0.0001 to 10 mol with respect to 1 mol of the basic catalyst.

(8) The process for producing according to any one of (5) to (7), wherein the phase-transfer catalyst is an onium salt, a crown ether, or a surfactant.

In description below, the α,α-bis(hydroxymethyl)alkanal represented by Formula (II) may be simply referred to as an α,α-bis(hydroxymethyl)alkanal and the α,α-bis(hydroxymethyl)alkanoic acid represented by Formula (III) may be simply referred to as an α,α-bis(hydroxymethyl)alkanoic acid in some cases.

The groups in the above formulas are defined as described below. Examples of the alkyl group include, for example, a linear or branched alkyl group having one to eighteen carbon atoms such as a methyl group, an ethyl group, a propyl group, an isopropyl group, a butyl group, an isobutyl group, a sec-butyl group, a tert-butyl group, a pentyl group, a hexyl group, a heptyl group, an octyl group, a nonyl group, a decyl group, a dodecyl group, and an octadecyl group. In particular, an alkyl group with one to six carbon atoms is preferable and the ethyl group is more preferable. As the cycloalkyl group include, for example, a cycloalkyl group with three to eight carbon atoms such as a cyclopropyl group, a cyclobutyl group, a cyclopentyl group, a cyclohexyl group, a cycloheptyl group, and a cyclooctyl group. Examples of the aryl group include a phenyl group, a naphthyl group, an anthranyl group, and the like.

Formaldehyde is preferably used in the form of an aqueous solution, more preferably in the form of an aqueous solution containing 5% to 60% of formaldehyde, and further more preferably in the form of an aqueous solution containing 30% to 55% of formaldehyde on a weight basis. To 1 mol of the aldehyde represented by Formula (I), the amount of formaldehyde used is preferably 0.3 to 1.7 mol, more preferably 0.6 to 1.5 mol, and further more preferably 0.9 to 1.3 mol.

Examples of the basic catalyst include basic inorganic compounds such as sodium hydroxide, potassium hydroxide, calcium hydroxide, sodium carbonate, potassium carbonate, sodium hydrogen carbonate, and potassium hydrogen carbonate; basic organic compounds such as triethylamine and tributylamine; and solid basic catalysts such as basic ion exchangers.

To 1 mol of the aldehyde represented by Formula (I), the amount of the basic catalyst used is preferably 0.001 to 0.3 mol and more preferably 0.01 to 0.2 mol.

Examples of the phase-transfer catalyst include an onium salt, a crown ether, a surfactant and the like.

Examples of the onium salt include an ammonium salt, a phosphonium salt, an arsonium salt and the like. In particular, the ammonium salt, the phosphonium salt and the like are preferable.

Examples of the ammonium salt include tetramethylammonium bromide, tetrabutylammonium bromide, benzyltrimethylammonium bromide, cetyldimethylethylammonium bromide, cetyltrimethylammonium bromide, cetyltrimethylammonium chloride, and the like.

Examples of the phosphonium salt include tetrabutylphosphonium bromide, tetraphenylphosphonium bromide and the like.

Examples of the arsonium salt include tetraphenylarsonium chloride and the like.

Examples of the crown ether include dibenzo-18-crown-6, dicyclohexyl-18-crown-6,18-crown-6,15-crown-5 and the like.

Examples of the surfactant include an anionic surfactant, a cationic surfactant, an amphoteric surfactant, a nonionic surfactant, and a compound surfactant. In particular, the anionic surfactant is preferable.

Examples of the anionic surfactant include carboxylates, sulfonates, sulfate esters, phosphate esters and the like. In particular, the anionic surfactant include sodium dodecylsulfate, lithium dodecylsulfate, lithium 3,5-diiodosalicylate, tris(hydroxymethyl)aminomethane dodecylsulfate, sodium cholate, N-lauroylsarcosine, sodium N-dodecanoilsarcosinate and the like.

Examples of the amphoteric surfactant include betaines, aminocarboxylic acids, and imidazoline derivatives.

Example of nonionic surfactant include an ether type, an ether-ester type, an ester type, and a nitrogen-containing type. A fluorine-containing surfactant, a reactive surfactant, a polymer flocculant, an ore flotation agent and the like may be also be used as the nonionic surfactant.

These types of phase-transfer catalyst may be used alone or in combination of two or more types.

To 1 mol of the aldehyde represented by Formula (I), the amount of the phase-transfer catalyst used is preferably 0.0001 to 0.1 mol and more preferably 0.001 to 0.01 mol.

To 1 mol of the basic catalyst, the amount of the phase-transfer catalyst used is preferably 0.0001 to 10 mol, more preferably 0.001 to 1 mol, and further more preferably 0.01 to 0.5 mol.

The temperature of the reaction is preferably 10° C. to 100° C., more preferably 30° C. to 80° C., and further more preferably 40° C. to 70° C. The time of the reaction is not particularly limited and is preferably 10 minutes to 12 hours, more preferably 20 minutes to 8 hours, and more preferably 30 minutes to 5 hours.

The reaction may be performed in the presence of a solvent. The solvent is not particularly limited as long as it is inert to the reaction. Examples of the solvent include water, methanol, ethanol and the like.

After the reaction is finished, the reaction mixture is subjected to extraction and/or distillation, whereby the α,α-bis(hydroxymethyl)alkanal can be refined.

The α,α-bis(hydroxymethyl)alkanal obtained may be oxidized into the α,α-bis(hydroxymethyl)alkanoic acid or reduced into a trimethylolalkane.

Examples of a process for oxidizing the obtained α,α-bis(hydroxymethyl)alkanal into the α,α-bis(hydroxymethyl)alkanoic acid include a process for oxidizing the α,α-bis(hydroxymethyl)alkanal with hydrogen peroxide (U.S. Pat. No. 3,312,736), a process for oxidizing the α,α-bis(hydroxymethyl)alkanal with hydrogen peroxide in the presence of a catalyst containing cerium, titanium, zirconium or the like (Japanese Published Examined Patent Application No. 45430/1995), a process for oxidizing the α,α-bis(hydroxymethyl)alkanal with i-butylhydroperoxide (Journal of Synthetic Organic Chemistry, Japan, vol. 36, p. 1095 (1978)), and a process for oxidizing the α,α-bis(hydroxymethyl)alkanal with air or oxygen (Japanese Published Unexamined Patent Application No. 100349/1999).

In the process for oxidizing the α,α-bis(hydroxymethyl)alkanal with air or oxygen, a reactive solvent is preferably used. Examples of the reactive solvent include acetates such as ethyl acetate and butyl acetate; lower alcohols such as methanol, ethanol, n-propyl alcohol, isopropyl alcohol, n-butyl alcohol, and isobutyl alcohol; ketones such as acetone, methyl ethyl ketone, and methyl isobutyl ketone;

and water and the like. The temperature of the oxidation is preferably from 40° C. to 100° C. The concentration of the α,α-bis(hydroxymethyl)alkanal in a reaction solution is preferably 50% or less on a weight basis.

The amount of air or oxygen used is preferably greater than or equal to the theoretical amount required to oxidize the α,α-bis(hydroxymethyl)alkanal.

After the oxidation is finished, the obtained reaction solution is concentrated. The resulting reaction solution is mixed with a solvent such as an acetate including ethyl acetate or a ketone including acetone and then the obtained α,α-bis(hydroxymethyl)carboxylic acid subjected to crystallization, whereby a target product is obtained.

Examples of the process for producing trimethylolalkane by reducing the α,α-bis(hydroxymethyl)alkanal include a process for reducing the α,α-bis(hydroxymethyl)alkanal in the presence of a catalyst containing Cu, Ni, Pd, Pt or the like.

The α,α-bis(hydroxymethyl)alkanal and the α,α-bis(hydroxymethyl)alkanoic acid are useful as a starting material for polymers such as polyurethane, polyester, and epoxy resins.

A process for producing of the present invention is industrially useful because the α,α-bis(hydroxymethyl)alkanal can be obtained with high efficiency and high selectivity and since the amount of formaldehyde remaining after the completion of reaction is small due to its high aldehyde conversion, the load of a step of refining a final product will be low even if the α,α-bis(hydroxymethyl)alkanal is subjected to oxidation or reduction without removing formaldehyde.

BEST MODE FOR CARRYING OUT THE INVENTION

Example 1

Into a 300-mL round-bottomed flask equipped with a reflux condenser, 72.1 g (1 mol) of n-butylaldehyde was fed. Furthermore, 81.2 g (1 mol) of 37% formaldehyde, 10.6 g (0.02 mol) of a 20% aqueous solution of sodium carbonate, and 0.58 g (0.002 mol) of sodium dodecylsulfate were then fed into the flask. These reactants were subjected to reaction at 60° C. for one hour. In the reaction, the conversion of formaldehyde was 97.5% and the yield of α,α-bis(hydroxymethyl)butanal was 67.2% on the basis of formaldehyde. The yield of 2-ethylacrolein was 13.2% on the basis of n-butylaldehyde.

Example 2

Into a 300-mL round-bottomed flask equipped with a reflux condenser, 72.1 g (1 mol) of n-butylaldehyde was fed. Furthermore, 97.4 g (1.2 mol) of 37% formaldehyde, 13.2 g (0.025 mol) of a 20% aqueous solution of sodium carbonate, and 0.58 g (0.002 mol) of sodium dodecylsulfate were then fed into the flask. These reactants were subjected to reaction at 60° C. for three hours. In the reaction, the conversion of formaldehyde was 92.6% and the yield of α,α-bis(hydroxymethyl)butanal was 70.0% on the basis of formaldehyde. The yield of 2-ethylacrolein was 10.1% on the basis of n-butylaldehyde.

Example 3

Into a 300-mL round-bottomed flask equipped with a reflux condenser, 72.1 g (1 mol) of n-butylaldehyde was fed. Furthermore, 81.2 g (1 mol) of 37% formaldehyde, 10.6 g (0.02 mol) of a 20% aqueous solution of sodium carbonate, and 0.68 g (0.002 mol) of tetrabutylphosphonium bromide were then fed into the flask. These reactants were subjected to reaction at 60° C. for one hour. In the reaction, the conversion of formaldehyde was 96.2% and the yield of α,α-bis(hydroxymethyl)butanal was 67.8% on the basis of formaldehyde. The yield of 2-ethylacrolein was 13.0% on the basis of n-butylaldehyde.

Comparative Example 1

Into a 300-mL round-bottomed flask equipped with a reflux condenser, 72.1 g (1 mol) of n-butylaldehyde was fed. Furthermore, 97.4 g (1.2 mol) of 37% formaldehyde and 13.2 g (0.025 mol) of a 20% aqueous solution of sodium carbonate were then fed into the flask. These reactants were subjected to reaction at 60° C. for three hours. In the reaction, the conversion of formaldehyde was 84.4% and the yield of α,α-bis(hydroxymethyl)butanal was 57.1% on the basis of formaldehyde. The yield of 2-ethylacrolein was 13.1% on the basis of n-butylaldehyde.

Results of Examples 1 to 3 and Comparative Example 1 are shown in Table 1.

TABLE 1

|  | Example 1 | Example 2 | Example 3 | Comparative Example 1 |
|---|---|---|---|---|
| Amount of n-butylaldehyde used (mol) | 1 | 1 | 1 | 1 |
| Amount of formaldehyde used (mol) | 1 | 1.2 | 1 | 1.2 |
| Amount of basic catalyst used (mol) | Sodium carbonate (0.02) | Sodium carbonate (0.025) | Sodium carbonate (0.02) | Sodium carbonate (0.025) |
| Amount of phase-transfer catalyst used (mol) | Sodium dodecylsulfate (0.002) | Sodium dodecylsulfate (0.002) | Tetrabutylphosphonium bromide (0.002) | None |
| Conversion of formaldehyde (%) | 97.5 | 92.6 | 96.2 | 84.4 |
| Yield of α,α-bis(hydroxymethyl)butanal (%) (on the basis of formaldehyde) | 67.2 | 70.0 | 67.8 | 57.1 |
| Yield of 2-ethylacrolein (%) (on the basis of n-butylaldehyde) | 13.2 | 10.1 | 13.0 | 13.1 |

Table 1 shows that the process of Examples 1 to 3 are superior in both the conversion of formaldehyde and the yield of a target product as compared to the process of Comparative Example 1.

INDUSTRIAL APPLICABILITY

The present invention provides a process for producing an α,α-bis(hydroxymethyl)alkanal in an aldehyde such as an aliphatic aldehyde with high efficiency because of the high conversion of formaldehyde.

What is claimed is:

1. A process for producing an α,α-bis(hydroxymethyl) alkanal represented by Formula (II):

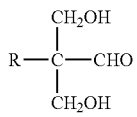
(II)

(wherein R represents an alkyl group, a cycloalkyl group, or an aryl group) which comprises reacting an aldehyde represented by Formula (I):

(I)

with formaldehyde in the presence of a basic catalyst and a phase-transfer catalyst.

2. The process according to claim 1, wherein the amount of formaldehyde used is in the range of 0.3 to 1.7 mol with respect to 1 mol of the aldehyde represented by Formula (I).

3. The process according to claim 1 or 2, wherein the amount of the phase-transfer catalyst used is in the range of 0.0001 to 10 mol with respect to 1 mol of the basic catalyst.

4. The process according to claim 1 or 2, wherein the phase-transfer catalyst is an onium salt, a crown ether, or a surfactant.

5. The process for producing an α,α-bis(hydroxymethyl) alkanoic acid represented by Formula (III):

(III)

(wherein R represents an alkyl group, a cycloalkyl group, or an aryl group) which comprises reacting an aldehyde represented by Formula (I):

(I)

with formaldehyde in the presence of a basic catalyst and a phase-transfer catalyst to obtain an α,α-bis(hydroxymethyl) alkanal represented by Formula (II):

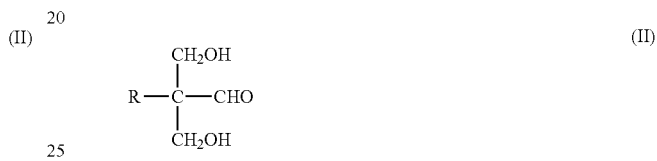
(II)

and oxidizing the obtained α,α-bis(hydroxymethyl)alkanal.

6. The process according to claim 5, wherein the amount of formaldehyde used is in the range of 0.3 to 1.7 mol with respect to 1 mol of the aldehyde represented by Formula (I).

7. The process according to claim 5 or 6, wherein the amount of the phase-transfer catalyst used is in the range of 0.0001 to 10 mol with respect to 1 mol of the basic catalyst.

8. The process according claim 5 or 6, wherein the phase-transfer catalyst is an onium salt, a crown ether, or a surfactant.

9. The process according to claim 3, wherein the phase-transfer catalyst is an onium salt, a crown ether, or a surfactant.

10. The process for producing according claim 7, wherein the phase-transfer catalyst is an onium salt, a crown ether, or a surfactant.

* * * * *

UNITED STATES PATENT AND TRADEMARK OFFICE
CERTIFICATE OF CORRECTION

| | | |
|---|---|---|
| PATENT NO. | : 7,247,755 B2 | Page 1 of 1 |
| APPLICATION NO. | : 10/563156 | |
| DATED | : July 24, 2007 | |
| INVENTOR(S) | : Shinichi Konishi et al. | |

It is certified that error appears in the above-identified patent and that said Letters Patent is hereby corrected as shown below:

COLUMN 8

Line 40, "for producing" should be deleted.

Signed and Sealed this

Eighteenth Day of December, 2007

JON W. DUDAS
*Director of the United States Patent and Trademark Office*